(12) United States Patent
Ghisu et al.

(10) Patent No.: US 10,873,328 B2
(45) Date of Patent: Dec. 22, 2020

(54) DRIVER CIRCUIT, CORRESPONDING ULTRASOUND APPARATUS AND METHOD

(71) Applicant: STMicroelectronics S.r.l., Agrate Brianza (IT)

(72) Inventors: Davide Ugo Ghisu, Milan (IT); Sandro Rossi, Pavia (IT); Andrea Gambero, Buscate (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 534 days.

(21) Appl. No.: 15/690,963

(22) Filed: Aug. 30, 2017

(65) Prior Publication Data

US 2018/0248544 A1 Aug. 30, 2018

(30) Foreign Application Priority Data

Feb. 24, 2017 (IT) .......................... 102017000021392

(51) Int. Cl.
*H03K 17/56* (2006.01)
*H03K 17/567* (2006.01)
(Continued)

(52) U.S. Cl.
CPC ............. *H03K 17/567* (2013.01); *A61B 8/54* (2013.01); *B06B 1/0215* (2013.01); *H03K 5/023* (2013.01); *H03K 5/08* (2013.01); *B06B 2201/77* (2013.01)

(58) Field of Classification Search
CPC ........... A61B 8/12; A61B 8/14; A61B 8/5207; A61B 8/4483; A61B 8/5269; A61B 8/54;
(Continued)

(56) References Cited

U.S. PATENT DOCUMENTS 3,555,888 A   1/1971  Brown
4,222,113 A   9/1980  Hansen
(Continued)

FOREIGN PATENT DOCUMENTS

CN   1851487 A    10/2006
CN   102668380 A   9/2012
(Continued)

OTHER PUBLICATIONS

Bianchi et al., "Analysis and Design of a High Voltage Integrated Class-B Amplifier for Ultra-Sound Transducers," *IEEE Transactions on Circuits and Systems—I: Regular Papers* 61(7):1942-1951, Jul. 2014.
(Continued)

*Primary Examiner* — Sibin Chen
(74) *Attorney, Agent, or Firm* — Seed IP Law Group LLP

(57) ABSTRACT

A driver circuit for driving, for example, ultrasonic transducers in medical equipment, such as ultrasound scanning equipment. The driver circuit includes first inputs receptive of a pulsed signal, second inputs receptive of an analog signal, an output for applying a pulsed drive signal or an analog drive signal to a load. A pair of output transistors of complementary polarities are positioned with their current paths in series between opposing supply lines with a connection point intermediate between the transistors of the pair of transistors. The connection point between output transistors is coupled to the output of the circuit. The control terminals of the output transistors, which are coupled together, may be coupled to the first inputs with the driver functioning as a pulser, or else coupled to the second inputs with the driver functioning as a linear driver.

20 Claims, 3 Drawing Sheets

(51) Int. Cl.
*H03K 5/08* (2006.01)
*A61B 8/00* (2006.01)
*B06B 1/02* (2006.01)
*H03K 5/02* (2006.01)

(58) Field of Classification Search
CPC .......... H03F 2200/03; H03F 2200/351; H03F 3/2171; H03F 3/2173; H03K 17/56; H03K 17/567; H03K 5/023; H03K 5/08; H03K 3/011; H03K 3/021; H03K 4/00; B06B 1/0215; B06B 2201/77
See application file for complete search history.

(56) References Cited

U.S. PATENT DOCUMENTS

| | | |
|---|---|---|
| 4,255,782 A | 3/1981 | Joyce |
| 4,321,485 A | 3/1982 | Morozowich et al. |
| 4,353,004 A | 10/1982 | Kleinschmidt |
| 4,357,690 A | 11/1982 | Kuroda et al. |
| 4,453,073 A | 6/1984 | Bredenkamp |
| 5,321,597 A | 6/1994 | Alacoque |
| 6,050,945 A | 4/2000 | Peterson et al. |
| 6,074,346 A | 6/2000 | Oppelt |
| 6,083,164 A | 7/2000 | Oppelt et al. |
| 6,316,993 B1 | 11/2001 | Hellums |
| 6,342,805 B1 | 1/2002 | Chen |
| 7,402,984 B1 | 7/2008 | Huang |
| 7,977,820 B2 | 7/2011 | Chu et al. |
| 8,447,046 B2 | 5/2013 | Huang et al. |
| 8,760,169 B2 | 6/2014 | Tang |
| 9,455,693 B2 | 9/2016 | Ghisu et al. |
| 9,544,965 B1 | 1/2017 | O'Neil et al. |
| 9,568,597 B2 | 2/2017 | Choy et al. |
| 9,979,363 B2 | 5/2018 | Ko et al. |
| 2005/0146371 A1 | 7/2005 | Wodnicki |
| 2005/0171431 A1 | 8/2005 | Petersen |
| 2005/0256409 A1 | 11/2005 | Pomata et al. |
| 2005/0275310 A1 | 12/2005 | Ripoll |
| 2006/0184033 A1 | 8/2006 | Cerofolini |
| 2007/0046143 A1 | 3/2007 | Blandino et al. |
| 2008/0150858 A1 | 6/2008 | Nishi et al. |
| 2010/0039159 A1 | 2/2010 | Otaka et al. |
| 2010/0113934 A1 | 5/2010 | Oguzman et al. |
| 2010/0128898 A1 | 5/2010 | Wong |
| 2012/0250462 A1 | 10/2012 | Franchini et al. |
| 2012/0313689 A1 | 12/2012 | Bottarel et al. |
| 2013/0170321 A1 | 7/2013 | Haider et al. |
| 2014/0085761 A1 | 3/2014 | Croft |
| 2014/0312954 A1 | 10/2014 | Ghisu et al. |
| 2015/0117675 A1 | 4/2015 | Jennings et al. |
| 2015/0181352 A1 | 6/2015 | Astgimath et al. |
| 2015/0281836 A1 | 10/2015 | Nguyen et al. |
| 2015/0318829 A1 | 11/2015 | Astgimath |
| 2018/0156903 A1 | 6/2018 | Pattipaka et al. |
| 2018/0226964 A1 | 8/2018 | Terenzi et al. |
| 2018/0248544 A1 | 8/2018 | Ghisu et al. |
| 2018/0271493 A1 | 9/2018 | Jensen et al. |
| 2019/0209139 A1 | 7/2019 | Petersen |

FOREIGN PATENT DOCUMENTS

| | | |
|---|---|---|
| CN | 102802535 A | 11/2012 |
| CN | 103229418 A | 7/2013 |
| CN | 103716017 A | 4/2014 |
| CN | 106140592 A | 11/2016 |
| WO | 2011/079881 A1 | 7/2011 |

OTHER PUBLICATIONS

Tripath Technology, Inc., "TAA4100—Four Channel Class-T Digital Audio Amplifier Using Digital Power Processing (DPP™) Technology," MAX14807, Preliminary Information, Revision 0.97, Apr. 2005, 20 pages.

Elmos Semiconductor AG, "Signal Conditioning IC for Directly driven ultrasonic sensors," production data sheet, document No. E524.07, QM-No. 25DS0118E.02, 2015, 39 pages.

DRIVER CIRCUIT, CORRESPONDING ULTRASOUND APPARATUS AND METHOD

BACKGROUND

Technical Field

The description relates generally to electronic driver circuits and one or more embodiments relate to electronic driver circuits usable, for example, in ultrasonic transmission channels and may be applied, for example, to ultrasound scanning equipment.

Description of the Related Art

Ultrasound scanning systems, such as those used in the medical field, can provide the presence of an ultrasonic transmission channel having the function of electrically stimulating a transducer (for example an ultrasound generator made of piezoelectric material or of the capacitive type) connected to its output during a transmit phase. Conversely, during a receive phase, the channel receives the echo of the transmitted wave from the transducer transferring it to the receiver circuitry and processing of the signal.

The role of transforming in a precise manner a given low-voltage signal into a high-voltage signal may be assigned to a driver circuit. Such systems may also provide for the echo received to be subjected to analysis based on the harmonics of the transmitted signal.

It is desirable for the driver circuit to be able to implement a correct excitation within the band of the active element introducing a low level of distortion, for example, generating signals that are symmetrical with respect to a reference voltage (GND), thus both negative and positive output voltages symmetrical with respect to the reference voltage (GND).

The drivers may be essentially ascribed to two basic (macro)categories: linear drivers and pulsed drivers, the latter also being known as pulsers.

In a linear driver, the circuit replicates at high voltage an (arbitrary) analog signal at low voltage. This category of driver may be based on an operational amplifier and allows the excitation of the active element within a band to be optimized, also allowing the handling of the probe, the signal to be smoothed in amplitude between elements of the same probe and offering a high level of flexibility in the excitation algorithms. A linear driver can also have certain drawbacks, such as the power dissipation, some integration issues, the occupation in area and, as a result, a high cost per channel. For this reason, linear drivers are currently used above all in high-end applications and with circuit topologies predominantly using discrete components.

In a pulsed driver or pulser, the circuit allows the high-voltage output to be taken to a given voltage level corresponding to a power supply to this circuit. This type of driver may comprise simple half-bridges, for example (also considering the reference ground as possible voltage level) three- or five-level systems, in which one or two half-bridges act on the output node. This solution can offer advantages for example in terms of high-level integration, reduced power dissipated by the circuit, limited occupied area and low cost per channel, but also drawbacks in terms of flexibility or optimization of the excitation of the active element. Pulsed drivers are currently used above all in standard or low-end systems and, considering the power dissipation, in CW (continuous wave) applications in which the active element is continuously stimulated.

The amplifier TAA4100 available from Tripath Technology, Inc. of 2560 Orchard Parkway, San Jose, Calif. 95131 (USA), the product MAX14807 available from Maxim Integrated of 160 Rio Robles, San Jose, Calif. 95134 (USA), the article by D. Bianchi et al.: "Analysis and Design of a High Voltage Integrated Class-B Amplifier for Ultra-Sound Transducers," IEEE Transactions on Circuits and Systems, Vol. 61, No. 7, July 2014, pp. 1942-1951, as well as U.S. Pat. No. 7,977,820 B2 exemplify prior art that refers to the scenario outlined hereinabove.

BRIEF SUMMARY

The claims form an integral part of the technical teachings put forward here in relation to one or more embodiments.

One or more embodiments may allow the functions of linear and pulsed drivers to be integrated into a single circuit solution that uses the same output power components, with the possibility of achieving one or more of the following advantages:
  use of only one output stage;
  economy in terms of area/cost;
  high symmetry of the output waveform in pulser mode;
  intrinsic robustness in the current feedback comparisons;
  possibility of avoiding the complete switch-off of the stage in the linear operation in order to avoid injection of charge during the switch-off and the (re)start-up of the same stage.

Advantageous aspects of one or more embodiments may comprise, aside from the possibility of using the same output power components in the two different modes (linear/pulsed):
  the possible re-use on the load of the drive current in the pulsed or pulser mode;
  the linear and pulser modes able to be connected to two different power supplies, with a potential addition for the pulser;
  an output stage configurable as an emitter follower supplied between an arbitrary pair of voltages +/−HV, with the consequent possibility of having output signals that are symmetrical with respect to a reference ground (GND).

BRIEF DESCRIPTION OF THE SEVERAL VIEWS OF THE DRAWINGS

One or more embodiments will now be described, purely by way of non-limiting example, with reference to the appended figures, in which.

DETAILED DESCRIPTION

In the description that follows, various details are illustrated that are specific to the aim of providing a deeper understanding of various exemplary embodiments according to the description. The embodiments may be obtained without one or more of the specific details, or with other methods, components, materials, etc. In other cases, known structures, materials or operations are not illustrated or described in detail so that the various aspects of the embodiments will not be rendered unclear. A reference to "an embodiment" in the framework of the present description is intended to indicate that a particular configuration, structure or feature described in relation to the embodiment is included in at least one embodiment. Accordingly, the phrases such as "in one embodiment," which may appear at various points of the present description, do not necessarily make reference to exactly the same embodiment. Furthermore, particular configurations, structures or features may be combined in any given appropriate manner in one or more embodiments.

The references used here are provided solely for convenience and thus do not define the scope of protection or the scope of the embodiments.

One or more embodiments are aimed at taking into account the fact that, if, on the one hand, circuit solutions able to unite within a single integrated structure both the drive functions (linear and pulsed) previously discussed are in increasing demand and more attractive for the market, on the other hand, making both the driver solutions coexist within the same circuit can lead to problems that are not easily solved.

Figure 1:
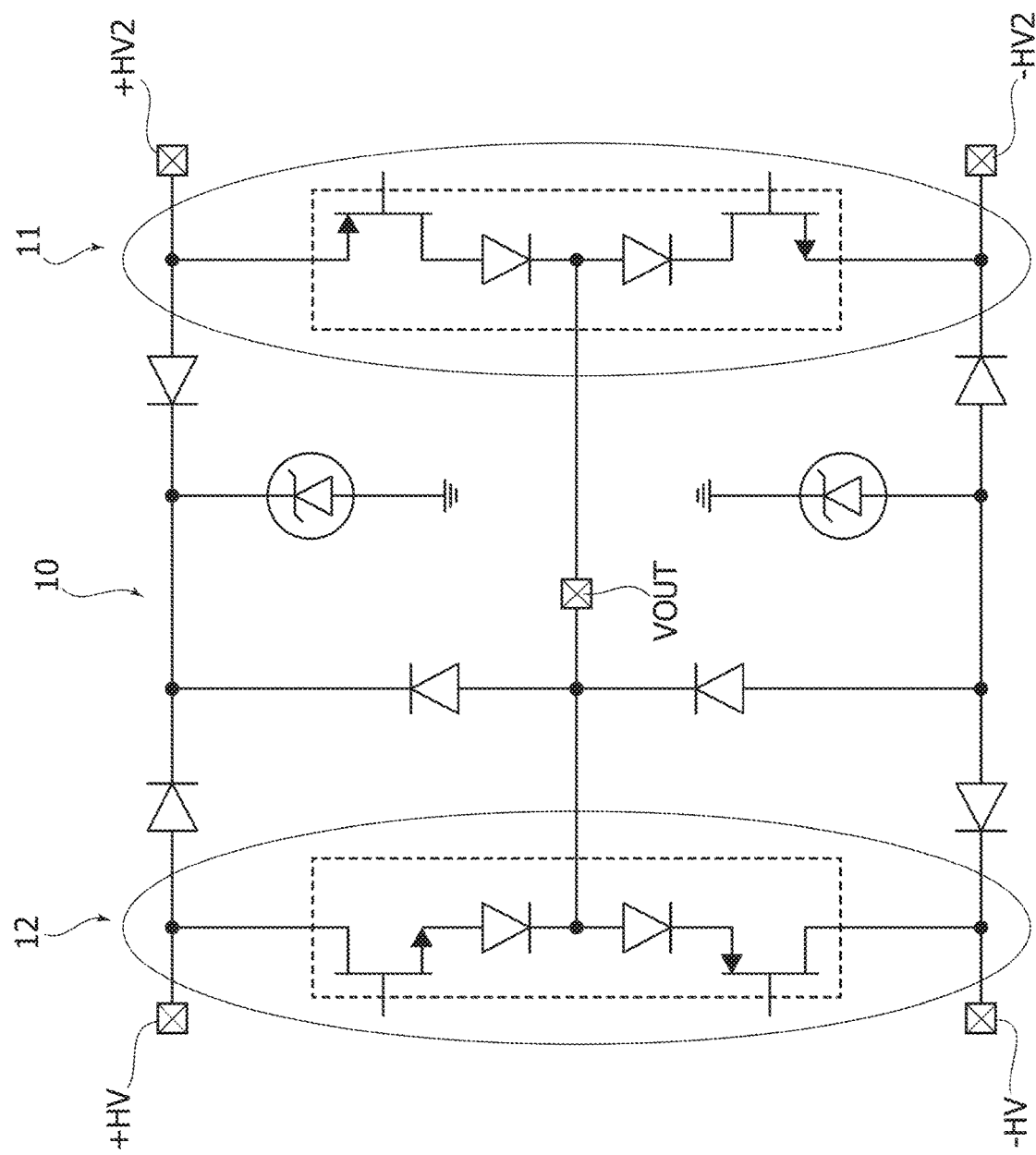
FIG. 1 is a circuit diagram of one possible implementation of a driver circuit.

For example, FIG. 1 exemplifies a possible implementation of a circuit 10 operating between two separate lines with a positive high voltage +HV/+HV2 and two separate lines with a negative high voltage −HV/−HV2 and that unites one output stage of the pulsed or pulser type 11 (on the right of the figure), one output stage of the linear type 12 (on the left of the figure), which in this instance is exemplified as an emitter follower, but may also adopt different solutions. Connected to the output node Vout, a clamp switch can be activated that is able to apply a reference voltage GND to the output of one or of the other stage Vout, with the possibility of forming for example a pulser with three levels.

Such a solution comprises various critical aspects from the circuit point of view:
the high-voltage power supplies are decoupled from each other with diodes in series with the output of both the pulser stage 11 and of the linear stage 12;
in order to allow the pulser stage 11 to operate, the diodes in series with the output of the linear stage are reverse biased in order to facilitate the turn-off of the output of the linear stage 12;
during the turn-on and the turn-off, glitches can be generated which, if transmitted onto the active element, may degrade the received signal;
the circuit that inverts the series diodes of the pulser stage 11 and of the linear stage 12 is not easy to implement;
the area occupied can be considerable;
on the output node VOUT a circuit is introduced for protection from possible current surges from the inductive component of the load intended to limit the (maximum) voltage on the components before they break down.

Figure 2:
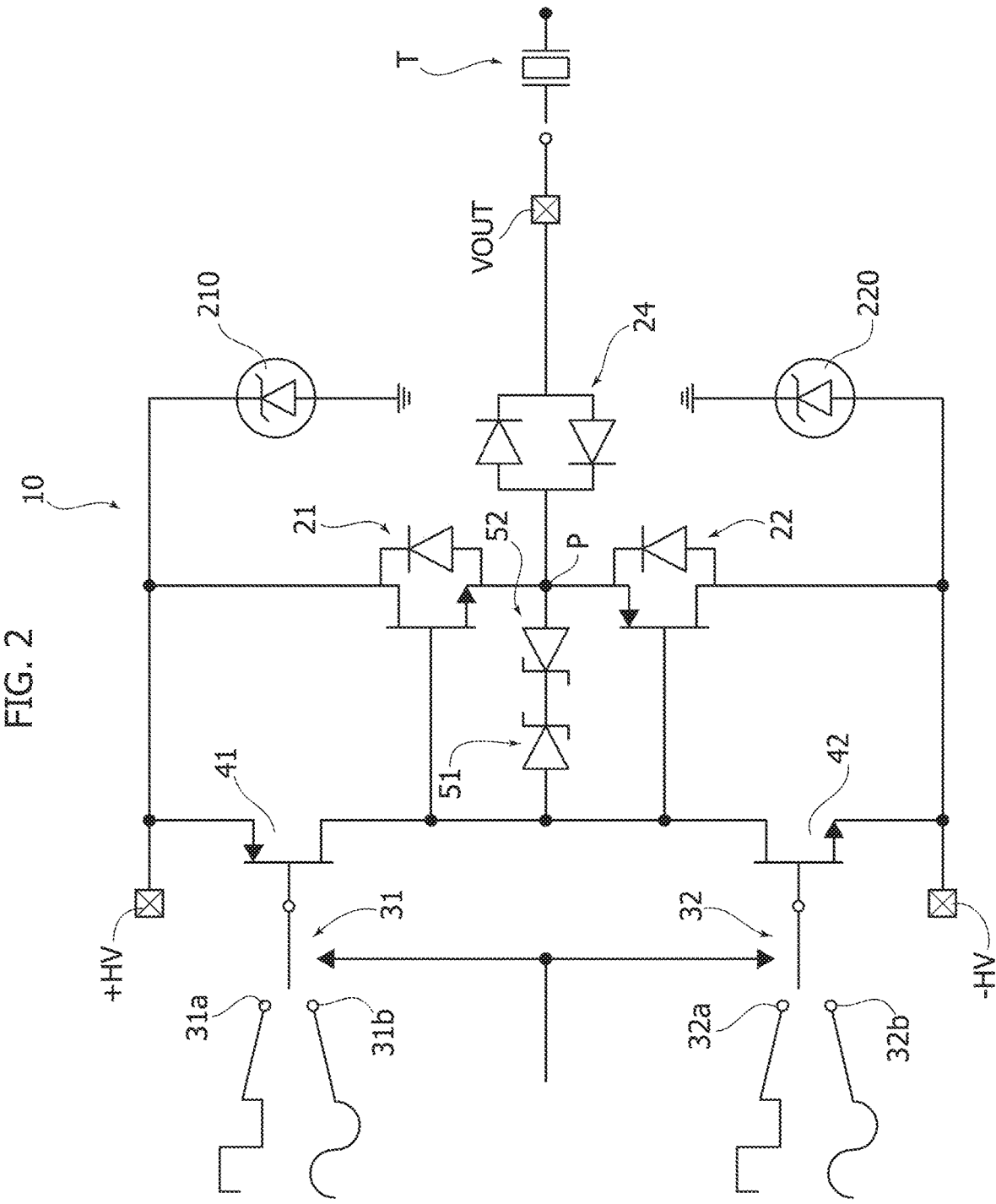
FIG. 2 is a circuit diagram of one possible implementation of embodiments according to the present disclosure.

FIG. 2 exemplifies a circuit solution according to one or more embodiments in which the same output power components may be used to drive an ultrasonic transducer T with the capability of carrying out various linear and pulsed driver functions, for example in an ultrasound scanning apparatus.

One or more embodiments are suitable to be used in ultrasound equipment, for example ultrasound scanning equipment, potentially in conjunction with the technical solutions described in various Patent applications for invention filed on the same date by the same applicant.

In the solution exemplified in FIG. 2, an output stage is present comprising two output transistors 21, 22 of complementary polarities (for example NMOS and PMOS) disposed with their current paths (source-drain in the case of field-effect transistors such as MOS transistors) in series with one another between the (maximum) positive and negative voltages +HV and −HV.

In one or more embodiments, the two transistors 21 and 22 may be disposed in an emitter-follower configuration with their current emission terminals (source, in the case of field-effect transistors such as MOS transistors) connected together at a node or point P in order to drive the output terminal VOUT, potentially via a pair of diodes (at low voltage) 24 coupled with opposite polarity, for example connected in anti-parallel (anode of one diode connected to the cathode of the other) for the purpose of decoupling the stray capacitance of the output stage during the receive phase.

In one or more embodiments, the control terminals (gate, in the case of field-effect transistors such as MOS transistors) of the transistors 21, 22 may be driven from a low-voltage input stage with voltage step-up circuits to the voltage +HV and −HV (not shown in the figures):
either digitally by a square wave,
or in an analog manner by an arbitrary signal In order to be able to generate as an output both a square wave between +HV and −HV (thus operating as a pulser, in pulsed mode) and an analog signal that "copies" the input signal (hence operating in linear mode), in such a mode, the output is able to be connected to an input stage via a feedback network.

In one or more embodiments, the choice of which input (31a, 32a—square wave or else 31b, 32b—analog) to apply to the control terminals of the transistors 21, 22 could be made by means of switches 31, 32 (for example electronic switches controlled by a signal LN_EN) able to be connected to the transistors 21, 22 via driver stages (for example MOSFET transistors, PMOS and NMOS) 41, 42, which are also able to be disposed, for example with their current paths (source-drain in the case of field-effect transistors such as MOS transistors) in series with one another between the voltages +HV and −HV, for example with the drains of the transistors 41 and 42 connected together.

It will be noted that both the disposition of connection of the transistors 41, 42 and the presence of the switches 31, 32 are here illustrated purely by way of example.

One or more embodiments may in fact adopt different connection configurations than those shown in the embodiment of FIG. 2.

One or more embodiments may provide the direct injection into the inputs of the circuit 10 (for example by means of voltage step-up circuits) of an analog signal (linear mode) or of a digital signal (pulser mode).

Although not considered as an essential feature, in one or more embodiments, the presence of a clamp (for example Zener diodes 210 and 220) may be provided acting between the power supply lines +HV and −HV and ground.

In one or more embodiments, between the connection node between the transistors 41 and 42 (for example between the drains, connected) and the connection node P between the transistors 21 and 22 which drives the output VOUT (for example between the source of the transistors 21 and 22) a clamp may be present comprising for example two Zener diodes 51, 52 connected in series with one another (cathode-cathode).

The clamp, here exemplified by the two Zener diodes 51, 52 (one or more embodiments may make use of other forms of implementation, known to those skilled in the art) can operate by making current flow towards the output VOUT limiting the voltage drop (for example between gate and source) on the transistors 21, 22 depending on the technology adopted for their fabrication.

In one or more embodiments, the clamp here exemplified by the two Zener diodes 51, 52, in the pulsed mode of operation (pulser) can also allow the drive current for the transistors 41 and 42 to be directed towards the output VOUT, hence towards the load, with each wave front generated by a power transistor of the N type and by its complement of the P type facilitating the achievement of the symmetry of the edges of the output signal. In one or more embodiments, as exemplified here, the transistors 41, 42 may in fact have polarities respectively opposing those of the transistors 21, 22, for example 21-NMOS with 41-PMOS and 22-PMOS with 42-NMOS.

Such a structure allows the recycling of the currents from the load directly onto the body-drain diodes of the transistors 21, 22 facilitating the overcoming of critical aspects linked to the fact that, as power transistors, the transistors 21, 22 can have dimensions linked to the current driving the load.

In one or more embodiments, as exemplified here, the circuit 10 may be powered, both in pulser mode and in linear mode, by a single power supply (for example +HV/−HV).

In one or more embodiments, it is possible to act on the circuit 10 so as to use different power supply voltages, potentially able to give rise for example to a pulser solution with five levels or allowing the current consumptions to be limited.

Figure 3:
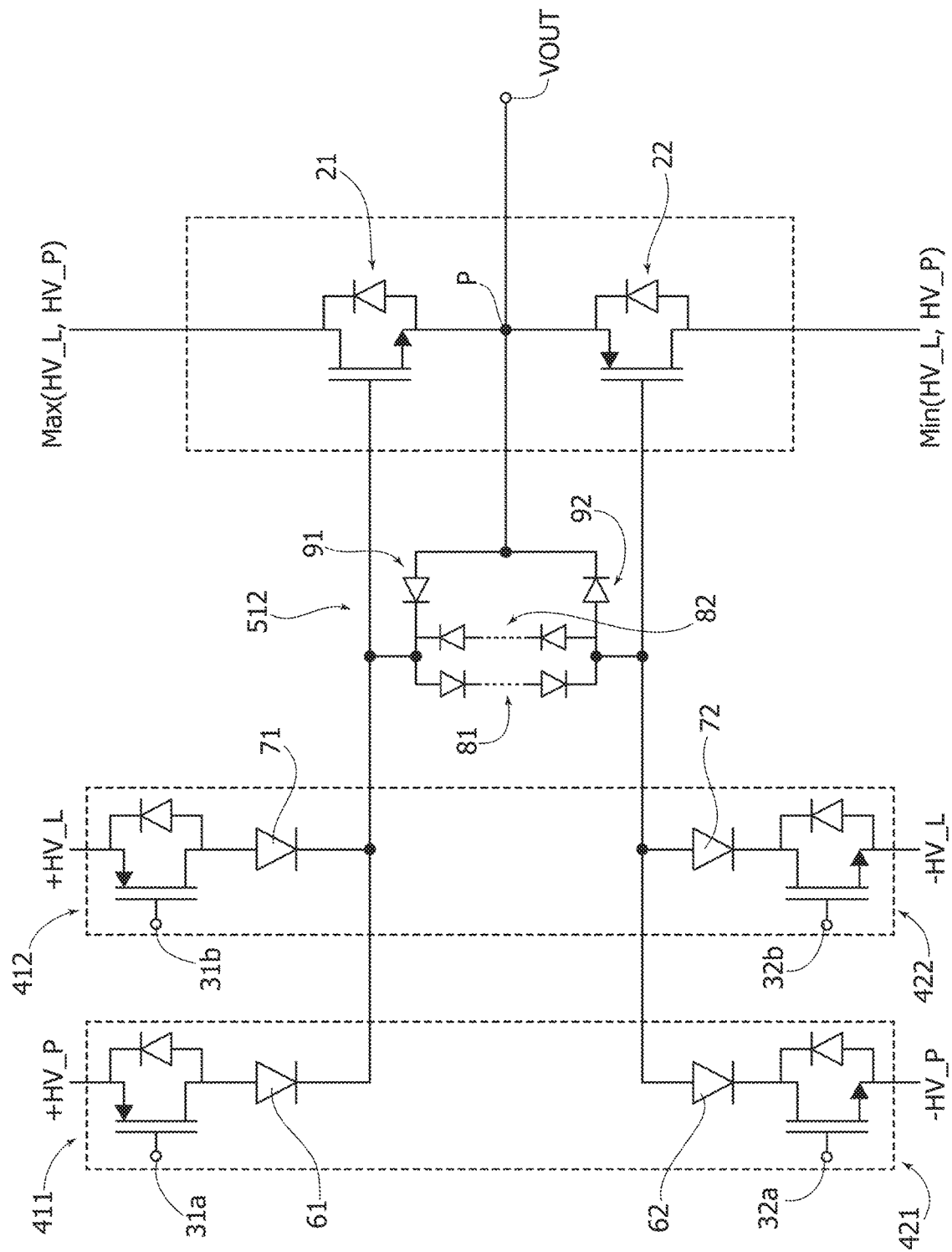
FIG. 3 is one example of a circuit diagram of one possible implementation of embodiments according to the present disclosure.

FIG. 3 exemplifies one or more embodiments based on such a development of the solution exemplified in FIG. 2.

In the circuit diagram in FIG. 3, the transistors 41 and 42 (for example PMOS and NMOS) in FIG. 2 are, so to speak, "split" into:

a first pair of transistors 411 and 421 (for example PMOS and NMOS) operating between voltages +HV_P and −HV_P, a second pair of transistors 412 and 422 (for example PMOS and NMOS) operating between voltages +HV_L and −HV_L.

The whole assembly with an input stage (not shown in the figures) is capable of driving for example:

the first pair of transistors 411 and 421 digitally, with a square wave (inputs 31a, 32a), the second pair of transistors 412 and 422 in an analog manner, with an arbitrary signal (inputs 31b, 32b).

In one or more embodiments, in the current paths of the transistors of the pair 411, 421 and of the pair 412, 422 respective pairs of diodes 61, 62 and 71, 72 may be present—for example coupled to the drain of the transistors 411, 421 and 412, 422—which are conducting (i.e., with forward biasing) when the respective pair of transistors is enabled and non-conducting (i.e., with reverse biasing) when the other pair of transistors is enabled.

In one or more embodiments, the possibility thus remains of connecting the power transistors 21, 22 to the higher of the voltages HV_L or HV_P, for example being able to use a lower voltage for the linear analog operation, exposed to a greater absorption of power, or of using in the CW mode power supply voltages in the pulser operation different from those used in the linear operation.

In one or more embodiments, it is possible to also add other driver stages (virtually any given number) connected to respective power supply values.

In one or more embodiments, the clamp solution 512 may be applied (alternative to the circuit 52) which solution is exemplified in FIG. 3 and comprises:

two strings of diodes 81, 82 disposed in anti-parallel (i.e., with anodes and cathodes turned in one way in the string 81 and in the opposite way in the string 82) between the control electrodes (gate, in the case of field-effect transistors) of the output power transistors 21 and 22, and two diodes 91, 92 each interposed between the control electrode of one of the transistors 21 and 22 and the point of connection (for example source) of these transistors 21 and 22 that drives the output VOUT, for example with the diodes 91, 92 disposed with their anodes and cathodes in such a manner as to be forward biased and to form respective conduction paths between the aforementioned point of connection and the control electrode of the transistor 21 (diode 91) and between the control electrode of the transistor 22 and the aforementioned point of connection P.

It will therefore be appreciated that various features discussed hereinabove with reference to any one of the figures may be applied, individually or in combination with one another, in embodiments exemplified in other figures, although not being specifically claimed in the description of these other figures.

One or more embodiments may therefore relate to a circuit (for example 10) comprising:

first inputs (for example 31a, 32a) receptive of a pulsed signal, second inputs (for example 31b, 32b) receptive of an analog signal, an output (for example VOUT) for applying to a load (for example T, which of itself may be an element distinct with respect to the embodiments) either a pulsed drive signal or an analog drive signal, a pair of transistors (for example MOSFET transistors 21, 22) of complementary polarity (for example NMOS and PMOS) positioned with their current paths (for example source-drain) in series between opposing supply lines (for example +HV, −HV in FIG. 2, or else Max(HV_L, HV_P), Min(HV_L,HV_P) in FIG. 3) with an intermediate connection point (for example P) between the transistors of the said pair of transistors, the transistors of the said pair having the said point of connection coupled to the said output as well as control terminals (for example gates) coupled to one another and couplable to the first inputs or else to the second inputs.

One or more embodiments may comprise a pair of diodes (for example 24) with opposing polarity, optionally in anti-parallel, interposed between the said connection point and the said output.

One or more embodiments may comprise switch circuitry (for example the electronic switches 31, 32 in FIG. 2 or the diodes 61, 62, 71, 72 in FIG. 3) acting between the control terminals of the transistors of the said pair of transistors and the first and second inputs so as to couple the control terminals of the transistors of the said pair of transistors to the first inputs or to the second inputs.

One or more embodiments may comprise a further pair of transistors (for example 41, 42 in FIG. 2) with complementary polarities (for example PMOS and NMOS) positioned with their current paths in series between the said opposing supply lines (for example +HV, −HV) with a respective intermediate connection point coupled to the control terminals of the transistors of the said pair of transistors, the control terminals of the transistors of the further pair of transistors being couplable (for example at 31, 32) to the first or to the second inputs. In one or more embodiments:

the opposing supply lines may comprise a first (for example +HV) and a second (for example −HV) supply line, the transistor (for example 21) of the said pair of transistors and the transistor (for example 41) of the said further pair of transistors coupled to the first supply line may have mutually complementary polarities (for example NMOS and PMOS), and the transistor (for example 22) of the said pair of transistors and the transistor (for example 42) of the said further pair of transistors coupled to the second supply line may have mutually complementary polarities (for example PMOS and NMOS).

One or more embodiments may comprise a clamp network (for example 51, 52) acting between the respective intermediate connection point between the transistors of the further pair of transistors and the intermediate connection point between the transistors of the said pair of transistors in order to transfer current with respect to the said output (VOUT).

In one or more embodiments, the said clamp network may comprise two Zener diodes of opposing polarity and optionally in series with one another (for example connected cathode-to-cathode).

One or more embodiments may comprise:

a first further pair of transistors (for example 411, 421) of complementary polarities (for example PMOS and NMOS), the first inputs receptive of a pulsed signal comprising the control terminals of the transistors of the first further pair of transistors, a second further pair of transistors (for example 412, 422) of complementary polarities (for example PMOS and NMOS), the second inputs receptive of an analog signal comprising the control terminals of the transistors of the second further pair of transistors, and switch circuitry, optionally diode means (for example 61, 62, 71, 72 in FIG. 3), for coupling to the control terminals of the transistors of the said pair of transistors the first (411, 421) or the second further pair of transistors.

In one or more embodiments:

the transistors of the first further pair of transistors (411, 421) may be coupled to a first pair of supply lines (for example +HV_P, −HV_P), and the transistors of the second further pair of transistors (412, 422) may be coupled to a second pair of supply lines (for example +HV_L, −HV_L).

In one or more embodiments, the first and the second further pair of transistors may each comprise:

a first transistor (for example 411, 412) couplable (for example by means of the diodes 61, 71) to the control terminal of one (for example 21) of the transistors of the said pair of transistors, and a second transistor (for example 421, 422) couplable (for example by means of the diodes 62, 72) to the control terminal of the other (for example 22) of the transistors of the said pair of transistors.

In one or more embodiments, the said switch circuitry may comprise:

a first diode (for example 61, 71) interposed between the first transistor of the first and second further pair of transistors and the control terminal of the said one of the transistors of the said pair of transistors, and a second diode (for example 62, 72) interposed between the second transistor of the first and second further pair of transistors and the control terminal of the other of the transistors of the said pair of transistors.

One or more embodiments may comprise a clamp network (for example 512) interposed between the control terminals of the transistors of the said pair of transistors and acting between the control terminals of the transistors of the said pair of transistors and the said output.

In one or more embodiments, this clamp network may comprise:

a first branch (for example 81, 82) interposed between the control terminals of the transistors of the said pair of transistors and optionally comprising two strings of diodes, the strings being positioned in anti-parallel with respect to one another, and a second branch (for example 91, 92) active between the control terminals of the transistors of the said pair of transistors and the said output and able to establish conduction paths between the said output and the control terminals of the transistors of the said pair of transistors.

An ultrasound apparatus according to one or more embodiments may comprise:

a driver device according to one or more embodiments, an ultrasonic transducer device (for example T) capable of converting an electric drive signal into an ultrasonic transmission signal, the said ultrasonic transducer device coupled to the said output of the driver device.

In one or more embodiments, a method may comprise:

providing a circuit according to one or more embodiments, coupling a load (for example T) to the output of the said circuit, and i) applying a pulsed signal to the first inputs of the circuit with the first inputs coupled to the control terminals of the transistors of the said pair of transistors, whereby a pulsed drive signal is present on the said load, or else ii) applying an analog signal to the second inputs of the circuit with the second inputs coupled to the control terminals of the transistors of the said pair of transistors, whereby an analog drive signal is present on the said load.

Keeping the basic principles of the disclosure, the particulars of implementation and the embodiments will be able to vary, even significantly, with respect to what has been illustrated purely by way of non-limiting example, without however straying from the scope of protection.

This scope of protection is defined by the appended claims.

The various embodiments described above can be combined to provide further embodiments. To the extent not inconsistent with the principles and teachings of the present disclosure, all the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A circuit, comprising:
   first inputs configured to receive a pulsed signal;
   second inputs configured to receive an analog signal;
   an output configured to apply to a load either a pulsed drive signal or an analog drive signal;
   a first pair of transistors of complementary polarity, each transistor of the first pair of transistors including a control terminal and a current path, and the first pair of transistors positioned with the current paths coupled in series between opposing supply lines with an intermediate connection point between the first pair of transistors, the connection point coupled to said output and the control terminals of the first pair of transistors coupled to one another and configured to be coupled to one of the first inputs or the second inputs.

2. The circuit according to claim 1, further comprising a pair of diodes of opposing polarity interposed between said connection point and said output.

3. The circuit according to claim 2, wherein the pair of diodes comprises the pair of diodes coupled in anti-parallel.

4. The circuit according to claim 3, further comprising switch circuitry coupled between the control terminals of the transistors of the first pair of transistors and the first inputs and second inputs, the switching circuitry configured to couple the control terminals of the transistors of the first pair of transistors to the first inputs in a pulsed mode and to the second inputs in a linear mode.

5. The circuit according to claim 4, comprising at least one second pair of transistors of complementary polarity, each transistor of the second pair including a control terminal and a current path, and the first pair of transistors positioned with the current paths coupled in series between the opposing supply lines with an intermediate connection point between the second pair of transistors coupled to the control terminals of the transistors of the first pair of transistors, the control terminals of the transistors of the second pair of transistors configured to be coupled to the first inputs and to the second inputs.

6. The circuit according to claim 5, wherein the switch circuitry is further coupled to the control terminals of the transistors of the second pair of transistors and is further configured to couple the control terminals of the transistors of the second pair of transistors to the first inputs in the pulsed mode and to the second inputs in the linear mode.

7. The circuit according to claim 5, wherein:
the opposing supply lines comprise a first supply line and a second supply line;
one transistor of the first pair of transistors and one transistor of the second pair of transistors are coupled to the first supply line and are of mutually complementary polarity; and
the other transistor of the first pair of transistors and the other transistor of the second pair of transistors are coupled to the second supply line and are of mutually complementary polarity.

8. The circuit according to claim 7, further comprising a clamp network coupled between the intermediate connection point between the transistors of the further second pair of transistors and the intermediate connection point between the transistors of the first pair of transistors and configured to transfer current with respect to said output.

9. The circuit according to claim 8, wherein said clamp network comprises two Zener diodes of opposing polarity coupled in series with one another.

10. The circuit according to claim 1, further comprising:
a second pair of transistors of complementary polarity, each transistor of the second pair including a control terminal, the first inputs configured to receive the pulsed signal corresponding to the control terminals of the transistors of the second pair of transistors;
a third pair of transistors of complementary polarity, each transistor of the third pair including a control terminal, the second inputs configured to receive the analog signal corresponding to the control terminals of the transistors of the third pair of transistors; and
switch circuitry configured to couple to the control terminals of the transistors of the first pair of transistors, the second pair of transistors, and the third pair of transistors.

11. The circuit according to claim 10, wherein the transistors of the second pair of transistors are coupled to a first pair of supply lines; and
the transistors of the third pair of transistors are coupled to a second pair of supply lines.

12. The circuit according to claim 11, wherein the second pair of transistors and the third pair of transistors each comprise:
a first transistor configured to be coupled to the control terminal of one of the transistors of the first pair of transistors; and
a second transistor configured to be coupled to the control terminal of the other one of the transistors of the first pair of transistors.

13. The circuit according to claim 12, wherein said switch circuitry comprises:
a first diode interposed between the first transistor of the second and third pair of transistors and the control terminal of the one of the transistors of the first pair of transistors; and
a second diode interposed between the second transistor of the second and third pair of transistors and the control terminal of the other one of the transistors of the first pair of transistors.

14. The circuit according to claim 13, further comprising a clamp network interposed between the control terminals of the transistors of the first pair of transistors and coupled between the control terminals of the transistors of the first pair of transistors and said output.

15. The circuit according to claim 14, wherein the clamp network comprises:
a first branch interposed between the control terminals of the transistors of the first pair of transistors and comprising two diode strings, the strings being positioned in anti-parallel with respect to one another; and
a second branch interposed between the control terminals of the transistors of the first pair of transistors and said output to establish conductive paths between said output and the control terminals of the transistors of the first pair of transistors.

16. An ultrasonic apparatus, comprising:
a drive circuit including,
first inputs configured to receive a pulsed signal;
second inputs configured to receive an analog signal;
an output;
a pair of transistors of complementary polarity, each transistor including a control node and having a current path, the pair of transistors having the current paths coupled in series between opposing supply lines and having an intermediate node formed between the pair of transistors, the intermediate node coupled to the output and the control nodes of the pair of transistors coupled to one another and configured to be coupled to one of the first inputs in a pulsed mode of operation to provide a pulsed drive signal on the output or to the second inputs in a linear mode of operation to provide a linear drive signal on the output; and
an ultrasonic transducer device coupled to the output and configured to convert the drive signal provided on the output into an ultrasonic transmit signal.

17. The ultrasonic apparatus of claim 16, further comprising a switch means for coupling the control terminals of the transistors of said pair of transistors to the first inputs in the pulsed mode of operation and to the second inputs in the linear mode of operation.

18. A method, comprising:
applying a pulsed signal to control terminals of a pair of complementary transistors coupled in series between a first supply node and a second supply node, and having an interconnection node defined at an interconnection of the pair of complementary transistors;
generating a pulsed drive signal on the interconnection node in response to the pulsed signal;
applying an analog signal to the control terminals of said pair of complementary transistors;
generating an analog drive signal on the interconnection node in response to the analog signal; and
coupling the drive signal on the interconnection node to an output node configured to be coupled to an ultrasonic transducer.

19. The method of 18, wherein applying the pulsed signal to control terminals of the pair of complementary transistors comprises applying the pulsed signal to control terminals of complementary driver transistors coupled to the control terminals of the pair of complementary transistors, and wherein applying the analog signal to the control terminals of said pair of complementary transistors comprises applying the analog signal to the control terminals of the complementary driver transistors.

20. The method of claim 18, wherein coupling the drive signal on the interconnection node to the output node comprises coupling the interconnection node to the output node through a pair of anti-parallel diodes.

* * * * *

UNITED STATES PATENT AND TRADEMARK OFFICE
CERTIFICATE OF CORRECTION

PATENT NO. : 10,873,328 B2
APPLICATION NO. : 15/690963
DATED : December 22, 2020
INVENTOR(S) : Davide Ugo Ghisu It is certified that error appears in the above-identified patent and that said Letters Patent is hereby corrected as shown below:

In the Claims

Column 8, Line 65, Claim 1:
"signal;" should read, --signal; and--.

Column 9, Line 5, Claim 1:
"to said" should read, --to the--.

Column 9, Line 10, Claim 2:
"between said" should read, --between the--.

Column 9, Line 11, Claim 2:
"said output" should read, --the output--.

Column 9, Line 52, Claim 8:
"the further second" should read, --the second--.

Column 9, Line 55, Claim 8:
"said output" should read, --the output--.

Column 9, Line 56, Claim 9:
"wherein said" should read, --wherein the--.

Column 10, Line 21, Claim 13:
"wherein said" should read, --wherein the--.

Column 10, Line 35, Claim 14:
"said output" should read, --the output--.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,873,328 B2

Column 10, Line 43, Claim 15:
"and said" should read, --and the--.

Column 10, Line 44, Claim 15:
"between said" should read, --between the--.

Column 10, Line 48, Claim 16:
"circuit including" should read, --circuit, including--.

Column 10, Line 51, Claim 16:
"output;" should read, --output; and--.

Column 11, Line 2, Claim 17:
"coupling the control" should read, --coupling control--.

Column 11, Line 3, Claim 17:
"said pair" should read, --the pair--.

Column 11, Line 14, Claim 18:
"of said" should read, --of the--.

Column 12, Line 4, Claim 19:
"of 18" should read, --of claim 18--.

Column 12, Line 10, Claim 19:
"said pair" should read, --the pair--.